United States Patent [19]

DeBerry

[11] 4,119,909
[45] Oct. 10, 1978

[54] PULSED DC TRANSIENT CONDUCTIVITY MEASUREMENT SYSTEM
[75] Inventor: David W. DeBerry, Austin, Tex.
[73] Assignee: Radian Corporation, Austin, Tex.
[21] Appl. No.: 783,463
[22] Filed: Mar. 31, 1977
[51] Int. Cl.² .................................. G01N 27/42
[52] U.S. Cl. .......................... 324/30 R; 324/30 B; 324/65 R
[58] Field of Search ............... 324/29, 26, 30 R, 30 B, 324/65 R, 61 R, 61 QL; 137/5, 93

[56] References Cited
U.S. PATENT DOCUMENTS

| | | | |
|---|---|---|---|
| 3,287,638 | 11/1966 | Bolie | 324/30 B |
| 3,296,523 | 1/1967 | Haas | 324/65 R |
| 3,724,474 | 4/1973 | DeVale | 324/65 R |

Primary Examiner—M. Tokar
Attorney, Agent, or Firm—Browning, Bushman & Zamecki

[57] ABSTRACT

Methods and apparatus are disclosed herein for measuring the electrical conductivity of unknown fluid solutions. A constant current DC pulse having a very fast rise time is supplied to a test cell containing the unknown solution. By sampling the voltage across the test cell just prior to the application of the pulse and at a predetermined time during the application of the constant current pulse, a voltage difference is obtained which may be interpreted in terms of the conductivity of the unknown solution.

12 Claims, 5 Drawing Figures

PULSED DC TRANSIENT CONDUCTIVITY MEASUREMENT SYSTEM

BACKGROUND OF THE INVENTION

This invention relates to the measurement of electrical conductivity. More specifically, the invention relates to the measurement of the electrical conductivity of fluid solutions.

Prior art instrumentation for measuring the conductivity of solutions generally utilize an AC signal applied to a conductivity cell containing a pair of electrodes which are immersed in the test solution. The more accurate commercial instruments use an AC bridge design with the cell as one arm of the bridge and manual balancing to a null point. Instruments of this type are typified by U.S. Pat. No. 3,086,169.

Alternatively, other techniques have been used in the prior art which may be classified as steady state DC techniques. In the steady state DC techniques the potential drop between a pair of electrodes supplied with a steady state constant current from a constant current DC source is measured. In such systems the current required to provide a predetermined potential drop between a pair of measurement electrodes then provides a measurement of the conductivity of the solution in a test cell between the electrodes. Systems of this type are typified by U.S. Pat. No. 3,646,436.

All of these prior art techniques have difficulty with electrolysis of the test solution together will effects due to polarization of the test solution. The term polarization will be used here to designate all electrochemical voltage differences other than that due to the passage of the test current through the solution.

The present invention avoids many of the difficulties encountered in the use of prior art systems and in so doing provides a simple and economical means for measuring the conductivity of test solutions.

SUMMARY OF THE INVENTION

In accordance with the principles of the present invention methods and apparatus are provided for measuring the conductivity of fluid solutions using a transient DC pulse measurement system. In the system of the present invention, a test solution is placed in or continuously passed through a suitable sample cell having platinized platinum electrodes. The zero current voltage or potential difference between the electrodes is sampled by a sample and hold circuit. A constant current very fast rise time DC pulse is then applied to the test solution. At a very short time duration after the beginning of the DC pulse, a second sample and hold circuit samples the DC voltage drop across the test solution between the electrodes. The difference between the zero current voltage drop across the electrodes and the voltage drop across the electrodes during the application of the fast rise time constant current DC pulse is then representative of the conductivity of the fluid in the test solution. By making the sampling time interval of sufficiently short duration and occurring at a sufficiently short time after the initiation of the constant current DC pulse, errors due to electrolysis and polarization of the test solution are minimized. This technique may be termed a transient DC measurement technique as opposed to the AC techniques and steady state DC techniques of the prior art.

The present invention is best understood by reference to the following detailed description thereof when taken in conjunction with the accompanying drawings, in which;

DESCRIPTION OF THE PREFERRED EMBODIMENT

The conductivity measurement method of the present invention is based on the application of a brief constant current space wave DC pulse having a very fast rise time to a conductivity cell containing the test solution. The test cell voltage resulting from the fast rise time DC pulse is sampled for a short interval almost immediately, after the pulse application. (For example on the other 10 microseconds). The resistance or conductance of the test solution may then be obtained from the magnitude of this voltage as measured at the very short time after the application of the constant current pulse, the applied constant current and the cell constant of the conductivity measurement cell itself. The cell constant depends on the geometry of the test cell and the test electrodes and is usually measured or calibrated beforehand using a calibration solution having known conductivity.

The ohmic voltage due to the solution resistance occurs very rapidly upon the application of a constant current DC pulse. The estimated inherent time constant $\tau$ is given by equation 1.

$$\tau = \frac{\rho D}{4\pi (9 \times 10^{11})} \text{ seconds} \tag{1}$$

In equation 1, $\rho$ is the specific resistance (ohm cm.) and D is the dielectric constant of the solution. Taking the value of D approximately equal to 80 for aqueous solutions, the inherent time constant $\tau$ can vary over the extreme range of values of from about 60 picoseconds for a 1.0 molar potassium chloride solution ($\rho = 9$ ohm cm.) to about 7.0 microseconds for distilled water ($\rho = 10^6$ ohm cm.). For most applications the error due to incomplete ohmic voltage rise is small enough to be considered negligible if the sample of test cell voltage is measured approximately 10 microseconds or later after the initiation of the very fast rise time DC square wave pulse to the test solution. The measurement time can be made shorter for relatively conductive solutions if desired.

Figure 4A:
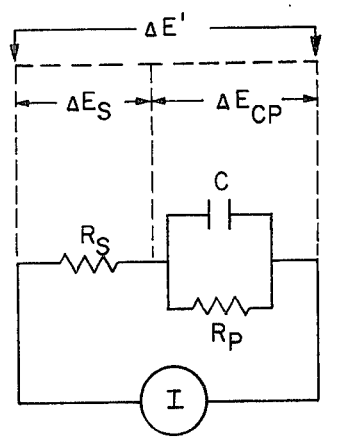
FIGS. 4a and 4b are equivalent circuit diagrams for one electrode and two electrode test cells of that type utilized in the present invention.

Prior to describing the measurement system of the present invention it would be convenient to provide a theoretical background for the measurement in accordance with the principles of the transient DC measurement technique of the invention. In this regard, reference is had to FIG. 4a which represents a simplified equivalent circuit for a metal electrode in contact with a solution. In the diagram of FIG. 4a $R_s$ is the resistance of the solution that is to be measured. C is the capacitance across the electrode solution double layer, and $R_p$ is an electrochemical reaction resistance. The following equations apply when a constant current DC pulse of magnitude I is applied to the circuit shown in FIG. 4a.

$$I = I_p + I_c \qquad (2)$$

$$I_c = C\frac{d}{dt}(\Delta E_{cp}) \qquad (3)$$

$$I_p = \frac{\Delta E_{cp}}{R_p} \qquad (4)$$

$$\Delta E = \Delta E_s + \Delta E_{cp} \qquad (5)$$

The voltage drop $E_s$ appears virtually instantaneously as noted previously with respect to the discussion of the inherent time constant $\tau$. The solution of equations 3, 4 and 5 for $\Delta E_{cp}=0$ when $t=0$ yields equation 6.

$$\Delta E_{cp} = IR_p[1 - e^{-t/R_pC}] \qquad (6)$$

Figure 4B:
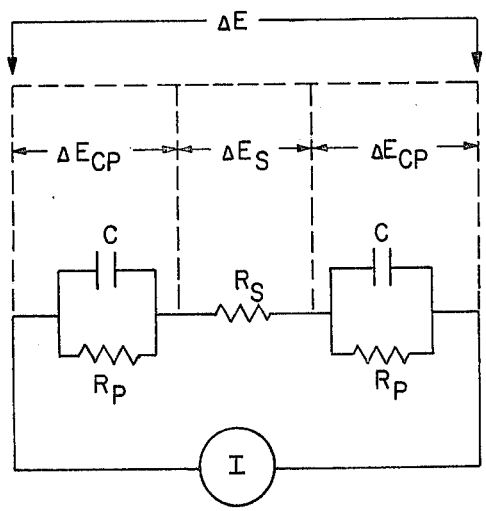

Referring now to FIG. 4b the introduction of the necessary second electrode results in another voltage component similar to that of equation 6. The total voltage drop across the test cell is then given by equation 7.

$$\Delta E = I[R_s + R_{p1}(1 - e^{-t/R_{p1}C_1}) + R_{p2}(1 - e^{-t/R_{p2}C_2})] \qquad (7)$$

Referring to equations 6 and 7 it is apparent that if the measurement time $t$ approaches zero, the cell voltage approaches the quantity desired to be measured, $I R_s$. Using a power series expansion for small values of the quantity $(t/R_pC)$ of the exponential function in the above equations and defining the apparent resistance R as $\Delta E/I$ yields equation 8.

$$R = R_s + \frac{t}{C_1} - \frac{t^2}{2R_{p1}C_1^2} + \ldots \qquad (8)$$
$$+ \frac{t}{C_2} - \frac{t^2}{2R_{p2}C_2^2} + \ldots$$

The inherent relative error in $R_s$ the solution resistance is given by equation 9.

$$\frac{R - R_s}{R_s} = \frac{1}{R_s}\left[\frac{1}{C_1} + \frac{1}{C_2}\right]t - \qquad (9)$$
$$\frac{1}{2R_s}\left[\frac{1}{R_{p1}C_1^2} + \frac{1}{R_{p2}C_2^2}\right]t^2 \ldots$$

When expressed in terms of the power series expansion it can be seen that the inherent error can be reduced to zero if the measurement is extrapolated to zero time. A finite measurement time, however, is required for practical commercial instrumentation. Therefore, it is necessary to define the relationship between the error, the measurement time and equivalent circuit parameters.

The solution resistance $R_s$ can be expressed in terms of the solution resistivity ($\rho$), the distance between the electrodes (L) and the effective cross-sectional area of the solution ($A_s$) as given in equation 10.

$$R_s = (\rho L/A_s) \qquad (10)$$

The electrode capacitance can similarly be expressed in terms of the capacitance per unit area of the electrode $\overline{C}$, the geometrical electrode area $A_e$ and the electrode roughness factor $f$ as given in equation 11.

$$C_i = f_i A_{ei} \overline{C}_i \qquad (11)$$

Generally $\overline{C}$ is at least 20 microfarads/cm² for metal electrodes. $\overline{C}$ can depend on electrode material, electrode potential, pH of the solution and electrolyte constituents. For platinum electrodes $\overline{C}$ may vary from 20 to over 500 microfarads/cm². The quantity $f$ may vary from near 1 for very smooth electrodes to several hundred for platinized platinum electrodes.

At high values of $\Delta E_{cp}$ the resistance $R_p$ is actually a series combination of a nonohmic charge transfer resistance and time dependent diffusion resistance. At short pulse times, however, the parallel capacitance serves to keep $\Delta E_{cp}$ small and diffusion gradients are not established since reactants are not depleted. For small values of $\Delta E_{cp}$, $R_p$ can be approximated by equation 12 as follows:

$$R_{pi} = (R_gT)/(n_i F A_{ei} f_i i^\circ) \qquad (12)$$

In equation 12 $R_g$ is the gas constant, T is the absolute temperature, $n$ is the stoichiometric number of electrons transferred, F is the Faraday constant, and $i^\circ$ is the exchange current. The exchange current $i^\circ$ is proportional to the concentration of the electroactive species and is measurable and tabulated for the different reactions. A typical value for the exchange current $i^\circ$ is $4 \times 10^{-3}$ amperes per square centimeter for the $Fe^{+2}/Fe^{+3}$ couple (0.01 molar solution in each). In this instance the specific electrode reaction resistance is 6.5 ohm cm² at 25° C.

Substituting equations 10, 11 and 12 into equation 9 yields equation 13 for the relative error E in terms of cell and electrochemical parameters.

$$E = \frac{A_s}{8L}\left[\left(\frac{1}{f_1 A_{e1}\overline{C}_1} + \frac{1}{f_2 A_{e2}\overline{C}_2}\right)t - \qquad (13)\right.$$
$$\left.\frac{F}{2R_gT}\left(\frac{n_1 i_1^\circ}{f_1 A_{e1}\overline{C}_1^2} + \frac{n_2 i_2^\circ}{f_2 A_{e2}\overline{C}_2^2}\right)t^2 + \ldots\right]$$

A numerical example for a typical solution using the values of the quantities of equation 13 as follows yields a relative error E as a function of time as follows:

$f_1 = f_2 = 1.0$ (smooth electrodes)
$A_{e1} = A_{e2} = A_s = 2$ cm²
L = 5 cm.
$\rho$ = 9 ohm cm. (1.0 M soln of KCl)
$\overline{C}_1 = \overline{C}_2 = 2 \times 10^{-5}$ Farad/cm²
$i_{1^\circ} = i_{1^\circ} = 4 \times 10^{-3}$ amp/cm²
T = 298° K.
$n_1 = n_2 = 1$
yielding:

$$E = 1.11 \times 10^3 [2t - 3.9 \times 10^3 t^2 + \ldots] \qquad (13a)$$

Equation 13a expresses the relative error as a function of time for the numerical example given above. It may be seen that if the measurement time is taken to be about 10 microseconds that this yields an error E of about 2.2%.

Thus, by initiating the sampling of a transient DC pulse at a measurement time of approximately 10 microseconds, according to the technique of the present invention the relative error is maintained at an acceptably small value. It is noteworthy that even for highly conductive solutions the error may be reduced substantially by using electrodes with higher roughness factors such as platinized platinum electrodes. The error decreases rapidly for less conductive solutions. Additional improvement in error minimization may be obtained through cell geometry optimization.

Figure 2:
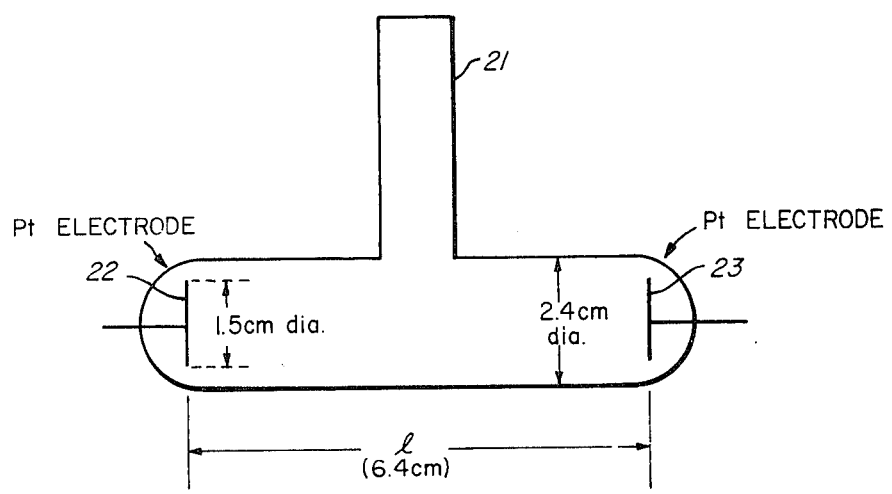
FIG. 2 is a schematic diagram showing a conductivity measurement cell as used in the system of the present invention.

In this regard, reference is had to FIG. 2 which shows a conductivity test measurement cell in accordance with the concepts of the present invention. A cylindrical cross-section glass envelope 21 having an inverted T-shape is provided with platinized platinum electrodes 22 and 23. The glass envelope 21 is filled with the test solution. The platinized platinum electrodes are circular discs in shape and have a diameter of approximately 1.5 centimeters. The electrodes 22 and 23 are spaced a distance (L) approximately 6.4 centimeters apart. This cell geometry represents a generally acceptable test cell geometry for use under commercial conditions in providing the desired accuracy of measurements while reducing the cost and complexity of the system to provide a relatively inexpensive commercially acceptable conductivity measurement system. Alternatively, rather than using a closed glass envelope a test cell of similar internal geometry and having open ends coupled by tubing to a pumping apparatus may be used. In this case the solution to be measured may be sampled, as for example, from a flow or pipe line, by pumping it continuously through the test cell while conducting the measurement.

Figure 1:
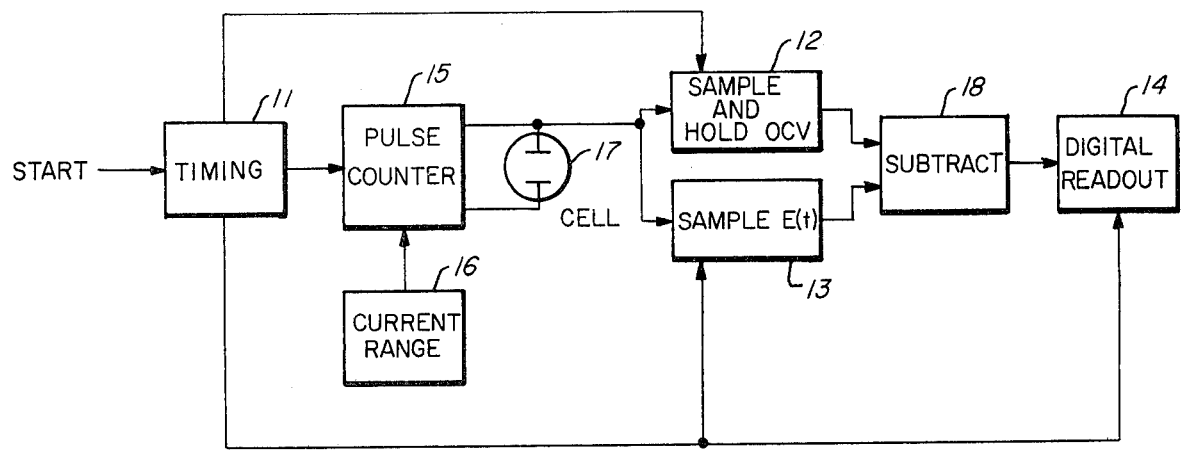
FIG. 1 is a schematic block diagram of a conductivity measuring system according to the concepts of the present invention.

Referring now to FIG. 1 a schematic block diagram of a conductivity measurement system in accordance with the concepts of the present invention is illustrated. Timing pulses from a timing source 11 which may be of conventional design and which represent relatively fast rise time DC pulses are provided to a first sample and hold circuit 12, a second sample and hold circuit 13, and a digital readout circuit 14. The timing pulses from the timing source 11 are also supplied to a pulse control circuit 15 which will be described in more detail subsequently. A current range decade selector switch 16 is used to provide a control to the pulse control circuit for controlling the magnitude of the constant current DC pulses which are generated by the pulse control circuit 15.

Very fast rise time, constant current, DC pulses are supplied from the pulse control circuit 15 and are applied to the test cell 17, which may be of the type previously described. The sample and hold circuit 12 upon receipt of a timing pulse from the timing source 11 (and prior to the application of the fast rise time DC constant current pulse to the test cell 17) samples the value of the voltage across the test cell prior to the generation of the constant current DC pulse. This value is supplied to a subtractor 18 which may be of conventional design.

Subsequent to the application of the DC pulse to the test cell 17, the second sample and hold circuit 13 samples the voltage between the electrodes of the test cell 17 and also supplies this sampled voltage to the subtract input of subtractor circuit 18. Upon receipt of both inputs from sample and hold circuits 12 and 13, the subtractor 18 subtracts the sampled voltage values and provides a representative difference value to a digital readout circuit 14. The digital readout circuit 14 displays these values by means of a digital display such as light emitting diode arrays, or the like.

Figure 3:
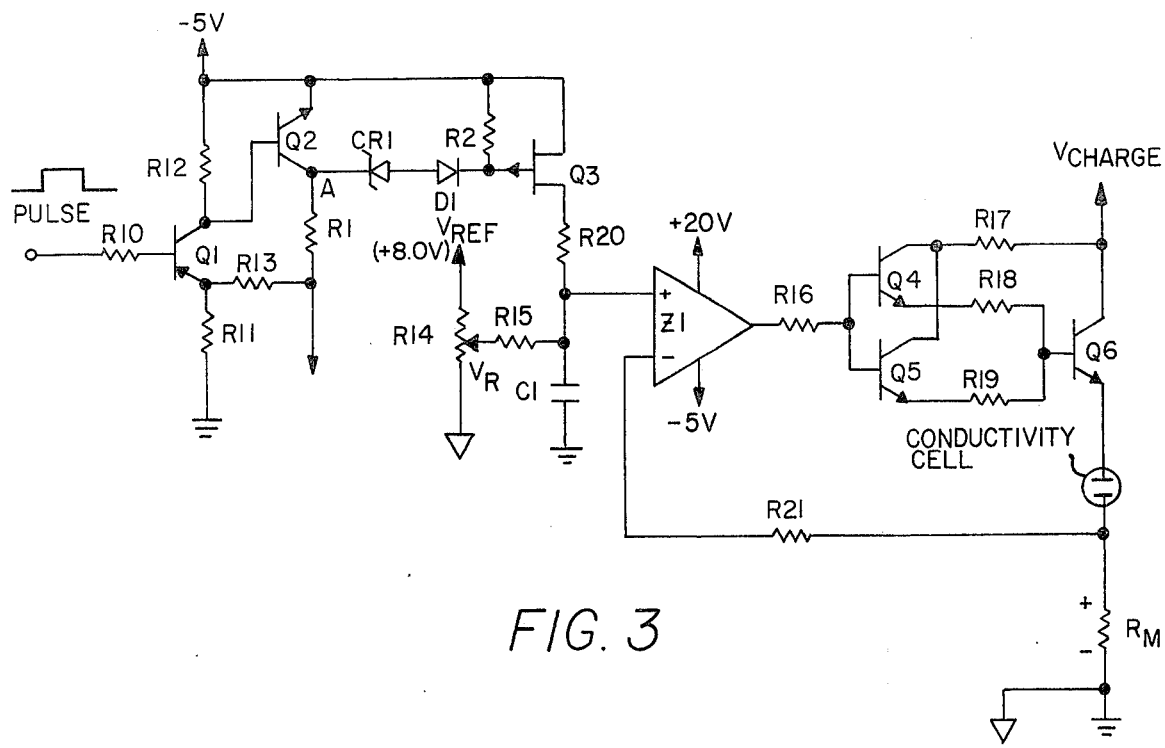
FIG. 3 is a curcuit diagram showing the current control section of the measurement system of the present invention.

Referring now to FIG. 3 the pulse control circuit 15 of FIG. 1 is illustrated in more detail. The pulse control circuit 15 basically comprises control transistors Q1, Q2 and Q3 and associated circuit elements, an inverting control operational amplifier Z1, a reference voltage source $V_R$ and associated circuit components, and measurement transistors Q4, Q5, and Q6 and their associated circuit elements.

Fast rise time square wave voltage pulses from the timing source 11 of FIG. 1 are input at the terminal labelled PULSE in FIG. 3. These pulses are coupled to the base of transistor Q1 via resistor R10. In the quiescent state (no pulse input) transistor Q1 is forward biased and conducts (since PULSE) is at ground potential. In this state the collector current of Q1 provides base current for transistor Q2 which saturates Q2. With transistor Q2 saturated the collector of Q2 and the cathode of Zener diode CRI (point A of FIG. 3) are at −5 volts. This condition results in the base of transistor Q3 being forward biased which turns transistor Q3 on. With Q3 on, the non-inverting input of operational amplifier Z1 goes to approximately −5 volts which, with the inverting input of Z1 being at ground potential, results in the output of Z1 being at a negative potential. This negative potential back biases transistors Q4 and Q5. In this condition no base current is provided for transistor Q6, which results in Q6 being cut off.

Upon receipt of a positive voltage timing pulse from timing pulse source 11 of FIG. 1, transistor Q1 becomes reversed biased and is cut off. With Q1 cut off, transistor Q2 has no source for base current and also cuts off. With transistor Q2 cut off point A begins to rise toward +20 volts. Due to the Zener action of CRI and the voltage drop in R1 and R2, the base of transistor Q3 is driven to approximately +9 volts. With its base at +9 volts Q3 is cut off which results in the reference potential VR (corresponding to the current range control 16 of FIG. 1) being applied to the non-inverting input of operational amplifier Z1. With the non-inverting input of Z1 more positive than the inverting input, the output of Z1 begins to go positive as the output of Z1 goes more positive, transistors Q4 and Q5 become forward biased and start to conduct. This condition provides base current for transistor Q6 which begins to conduct.

Current through transistor Q6 goes through the conductivity cell and measuring resistor Rm. The current through transistor Q6 and the voltage drop across Rm will increase until this voltage drop is equal to VR. The action of the operational amplifier Z1 will maintain the potential across Rm at this voltage for the duration of the positive voltage applied at PULSE.

Representative values of the circuit elements, together with circuit details are given in Table I below.

TABLE I

| R1 - 15K ohms | Q1 - type 2N5448 |
|---|---|
| R2 - 100K ohms | Q2 - type 2N5451 |
| R10 - 10K ohms | Q3 - type 2N5461 |
| R11 - 1K ohms | Q4 - type 2N2222 |
| R12 - 33K ohms | Q5 - type 2N2222 |
| R13 - 13K ohms | Q6 - type TIP35 |
| R15 - 220K ohms | CRI - type 1N758A |
| R16 - 620 ohms | DI - type 1N914 |
| R17 - 1.5K ohms | |
| R18 - 10 ohms | |
| R19 - 10 ohms | |
| R20 - 1K ohms | |
| R21 - 10K ohms | |

Summarizing the operation of the system of FIG. 1 for measuring the conductivity of a solution in the test cell 17, then;

(1) The open circuit voltage is sampled and held,
(2) a constant current pulse of a preselected reference voltage level is supplied to the cell,
(3) the cell voltage is sampled at a predetermined time (on the order of 10 microseconds) after initiation of the pulse, and
(4) the difference in the open circuit voltage and the cell voltage during the phase is formed and displayed.

It will be appreciated by those skilled in the art that various changes and modifications may be made to a conductivity measurement system such as that described without departing from the inventive concepts disclosed herein. It is the aim of the appended claims to cover all such variations and modifications as fall within the true spirit and scope of the invention.

I claim:

1. A method of measuring representations of the electrical conductivity of a fluid solution, comprising the steps of:
   locating a sample of fluid to be measured between a pair of measurement electrodes;
   sampling the zero current voltage drop between said measurement electrodes, generating a signal representative thereof and storing said representative signal;
   applying a very fast rise time DC constant current pulse to said measurement electrodes;
   sampling, at a predetermined time interval from the beginning of the application of said DC pulse, the constant current voltage drop between said electrodes and generating a signal representative thereof; and
   forming a difference function of said zero current voltage drop and said constant current voltage drop signals to generate a measurement signal representative of the electrical conductivity of a fluid to be measured.

2. The method of claim 1 wherein said predetermined time interval from the beginning of the application of said DC pulse is about 10 microseconds.

3. The method of claim 1 wherein said sampling steps are performed by sample and hold circuits.

4. The method of claim 1 wherein said constant current DC pulse is of predetermined selectable current magnitude.

5. The method of claim 1 and further including the steps of:
   correcting said measurement signal for cell and circuit constants of the measurement apparatus to thereby provide an absolute measurement of the conductivity of a fluid to be measured.

6. A system for measuring representations of the electrical conductivity of a fluid solution, comprising:
   a sample cell having a pair of measurement electrodes, for containing a fluid to be measured;
   means for sampling the zero current voltage drop between said measurement electrodes and for generating a signal representative thereof and for storing said representative signal;
   means for applying a very fast rise time constant current DC pulse to said measurement electrodes;
   means for sampling, at a predetermined time interval from the beginning of the application of said DC pulse, the constant current voltage drop between said electrodes and for generating a signal representative thereof; and
   means for forming a difference function of said zero current voltage drop and said constant current voltage drop signals to generate a measurement signal representative of the electrical conductivity of a fluid to be measured.

7. The system of claim 6 wherein said measurement electrodes comprise a pair of platinum electrodes.

8. The system of claim 6 wherein said measurement electrodes comprise a pair of platinized platinum electrodes.

9. The system of claim 8 wherein said measurement electrodes have a surface area of approximately 1.5 cm$^2$ each and are located approximately 6.4 cm. apart.

10. The system of claim 6 wherein said sampling means comprise first and second sample and hold circuits.

11. The system of claim 10 wherein said differencing means comprises a subtraction circuit.

12. The system of claim 6 wherein said sample cell is open ended and means are provided for moving said fluid to be measured continuously through said cell.

* * * * *